(12) United States Patent
Al-Jazaeri et al.

(10) Patent No.: US 10,849,617 B1
(45) Date of Patent: Dec. 1, 2020

(54) PIERCING FORCEPS

(71) Applicant: KING SAUD UNIVERSITY, Riyadh (SA)

(72) Inventors: Ayman Al-Jazaeri, Riyadh (SA); Rakan Nazer, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/788,163

(22) Filed: Feb. 11, 2020

(51) Int. Cl.
*A61B 17/062* (2006.01)
*A61B 17/28* (2006.01)
*A61B 17/04* (2006.01)
*A61B 17/34* (2006.01)
*A61B 17/00* (2006.01)

(52) U.S. Cl.
CPC ........ *A61B 17/062* (2013.01); *A61B 17/0482* (2013.01); *A61B 17/282* (2013.01); *A61B 17/2841* (2013.01); *A61B 2017/00429* (2013.01); *A61B 2017/3411* (2013.01)

(58) Field of Classification Search
CPC ... A61B 17/34; A61B 17/062; A61B 17/0482; A61B 17/0483; A61B 17/282; A61B 17/0469; A61B 2017/047; A61B 2017/0472; A61B 2017/00349
USPC ........................................ 606/139, 144, 145
See application file for complete search history.

(56) References Cited

U.S. PATENT DOCUMENTS

| | | | | |
|---|---|---|---|---|
| 2,738,790 | A * | 3/1956 | Todt, Sr. ................ | A61B 17/04 606/145 |
| 5,336,229 | A * | 8/1994 | Noda ............... | A61B 17/12013 606/139 |
| 6,984,237 | B2 | 1/2006 | Hatch et al. | |
| 7,879,048 | B2 * | 2/2011 | Bain .................. | A61B 17/0469 606/144 |
| 8,206,408 | B2 * | 6/2012 | Rebstock ........... | A61B 17/1611 606/167 |
| 8,469,974 | B2 | 6/2013 | Skinlo et al. | |
| 8,663,251 | B2 | 3/2014 | Burkhart et al. | |
| 9,662,105 | B2 | 5/2017 | Sinnott et al. | |
| 2004/0236353 | A1 | 11/2004 | Bain et al. | |
| 2005/0222589 | A1 | 10/2005 | Chu | |
| 2005/0251177 | A1 | 11/2005 | Saadat et al. | |
| 2006/0253144 | A1 | 11/2006 | Mikkaichi | |
| 2008/0077162 | A1 | 3/2008 | Domingo | |
| 2009/0287227 | A1 | 11/2009 | Newell et al. | |

(Continued)

*Primary Examiner* — Tuan V Nguyen
(74) *Attorney, Agent, or Firm* — Nath, Goldberg & Meyer; Richard C. Litman (57) ABSTRACT

A piercing forceps includes a dynamic handle and an L-shaped static handle connected to the dynamic handle. The static handle supports a primary slide with a clamping end and a secondary slide supporting needles. The dynamic handle may be operated to bring a distal end of the primary slide toward a distal end of the static handle to provide a tissue clamp. A trigger supported by the static handle may be operated to bring a distal end of the secondary slide toward the distal end of the static handle and primary slide, thus resulting in the needles of the secondary slide distally extending from the secondary slide to pierce tissue clamped between the static handle and primary slide. As a result, the tissue can be secured by being clamped between the static handle and primary slide, as well as by the needles of the secondary slide being inserted therethrough.

15 Claims, 13 Drawing Sheets

(56) References Cited

U.S. PATENT DOCUMENTS

| | | |
|---|---|---|
| 2010/0121352 A1 | 5/2010 | Murray et al. |
| 2010/0217151 A1 | 8/2010 | Gostout et al. |
| 2011/0224697 A1 | 9/2011 | Deitch et al. |
| 2012/0245598 A1 | 9/2012 | Brown et al. |
| 2014/0148828 A1 | 3/2014 | Ewers et al. |

* cited by examiner

PIERCING FORCEPS

BACKGROUND

1. Field

The present disclosure relates to tissue forceps, and in particular, to forceps which secure tissue through clamping and additionally by inserting needles through the tissue.

2. Description of the Related Art

The mitral valve is situated between the left atrium and left ventricle of the heart. It is located at the back of the heart and is overshadowed above by the aortic root and aortic valve. Adequate exposure to a valve is crucial for any successful cardiac valve intervention. This holds especially true for the mitral valve which is difficult to expose during surgery.

During cardiac valve intervention, surgical sutures are used to anchor a valve prosthesis or reshape the valve fibrous "annulus." Improperly placed sutures can result in misplacement of the prosthetic valve leading to a "para-valvular" leaking of blood from around the valve along with other complications. Conventionally, during a procedure, the valve annulus is surgically manipulated by pulling on it with a grasping forceps which sometimes can be difficult due to the hidden parts of the fibrous skeleton of the heart within the myocardium and its location behind other structures within the heart.

Multiple surgical approaches have been devised to access the mitral valve. The fibrous annulus of the mitral valve is usually embedded within 2-3 mm of the atrial myocardium. Depending on the site of the annulus, crucial cardiac structure and vessels pass in close proximity to the mitral fibrous annulus. Due to these constraints, it is difficult to gain proper exposure to the mitral valve and to place the surgical anchoring sutures inside the fibrous annulus without causing damage to other neighboring structures using the grasping forceps presently known in the art.

Thus, a forceps solving the aforementioned problems is desired.

SUMMARY

A piercing forceps includes a dynamic handle and an L-shaped static handle connected to the dynamic handle. The static handle supports a primary slide with a clamping end and a secondary slide supporting needles. The dynamic handle may be operated to bring a distal end of the primary slide toward a distal end of the static handle to provide a tissue clamp. A trigger supported by the static handle may be operated to bring a distal end of the secondary slide toward the distal end of the static handle and primary slide, thus resulting in the needles of the secondary slide distally extending from the secondary slide to pierce tissue clamped between the static handle and primary slide. As a result, the tissue can be secured by being clamped between the static handle and primary slide, as well as by the needles of the secondary slide being inserted therethrough.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present subject matter discloses a piercing forceps. The forceps includes a static handle connected to a primary slide and a secondary slide. A dynamic handle is connected to a distal end of the primary slide. A trigger, supported by the static handle, may be connected to the distal end of the secondary slide. The trigger can be operated to insert needles from the secondary slide into tissue clamped between the static handle and primary slide. As a result, the target tissue can be secured through clamping between the static handle and primary slide, as well as through the inserted needles of the secondary slide.

Figure 1:
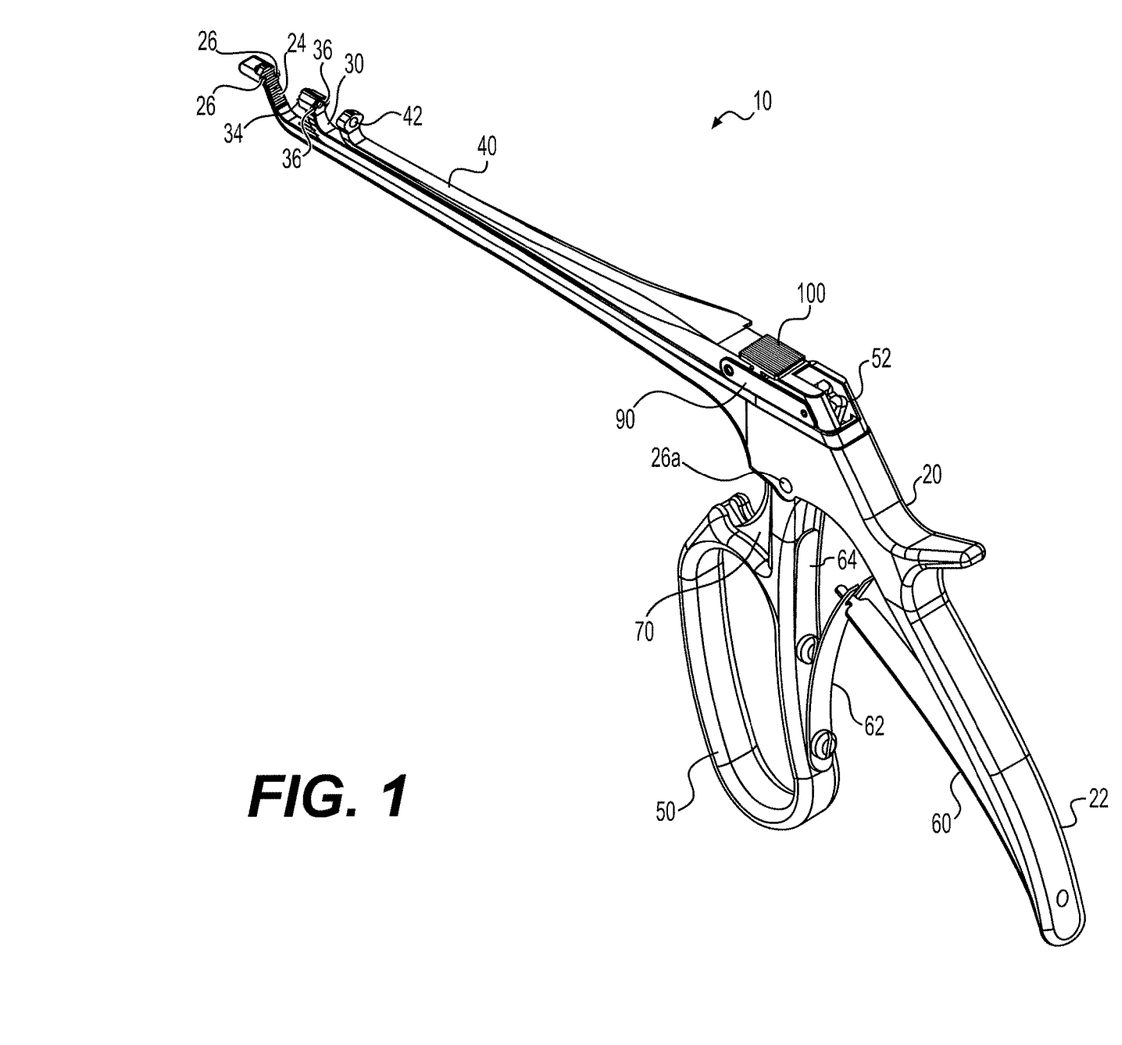
FIG. 1 is a perspective view of an embodiment of the piercing forceps.

FIG. 1 shows an embodiment of the piercing forceps 10 which includes a generally L-shaped static handle 20 having a proximal grip 22 and a distal tip 24 that includes a clamping surface. The static handle 20 may slidably support a primary slide 30 on its upper, generally horizontal surface. For example, the static handle 20 and primary slide 30 may be slidably connected by a guide rail system which allows the primary slide 30 to slide along a length of the static handle 30. A distal tip of the primary slide 30 may also include a clamping surface 34 aligned with the clamping surface at the distal tip 24 of the static handle 20 for clamping tissue therebetween or for holding a suture needle.

A dynamic handle 50 may be pivotally secured to the static handle 20 adjacent the proximal grip 22. The dynamic handle can be connected to the static handle 20 by a hinge pin 26a which can provide the pivotable connection between the two components 20, 50. An upper portion of the dynamic handle 50 includes a lever arm 52 which connects to the primary slide 30. A user can squeeze the dynamic handle 50 and the grip 22 together to cause the lever arm 52 to push the primary slide 30 distally toward the tip 24 of the static handle for clamping tissue or for holding a suture needle therebetween.

A secondary slide 40 may be slidably supported on an upper surface of the primary slide 30. The primary slide 30 and secondary slide 40 may be connected by a guide rail system which guides the secondary slide 40 along a length of the primary slide 30. A distal tip of the secondary slide 40 may include a needle cartridge port 42 for a needle cartridge 80 and two distally pointing needles (shown in FIGS. 9A and 9B). The needles can be aligned with needle guides 36 in the distal tip of the primary slide 30 and needle receptacles 26 in the static handle. A trigger 70, for operating the secondary slide 40, may be pivotally connected to the static handle 20 by hinge pin 29a. Accordingly, when the secondary slide 40 is manipulated to slide distally toward the distal tip 24 of the static handle using the trigger 70, the needles are inserted through the needle guides 36 and needle receptacles 26, and through any tissue clamped therebetween. An upper end of the trigger 70 may define a slot for accepting a pin spring 90 that is connected to the secondary slide 40. When the lower end of the trigger 70 is pulled proximally, the upper end may pivot distally, thus pushing the secondary slide 40 in a distal direction for piercing the clamped tissue with the attached needles.

The primary slide 30 may be held at a proximal position relative to the static handle 20 through the interaction between a static handle spring 60 and a dynamic handle spring 62. The dynamic handle spring 62 may extend proximally from the dynamic handle 50 and interlock with the distally extending static handle spring 60. The springs 60, 62 may produce a force that pushes the dynamic handle 50 away from the grip 22 of the static handle 20, and thereby, pushes the primary slide 30 proximally relative to the static handle 20. A trigger spring 64 may extend along a proximal side of the dynamic handle 50 to interact with a proximal side of the trigger 70. The trigger spring 64 may force the trigger 70 in a distal direction, thus pushing the secondary slide 40 in a proximal direction. The springs 60, 62, 70 may be designed with a stiffness capable of maintaining the slides 30, 40 in a proximal position which can be easily overcome by the gripping force of a user.

Figures 2A, 2B:
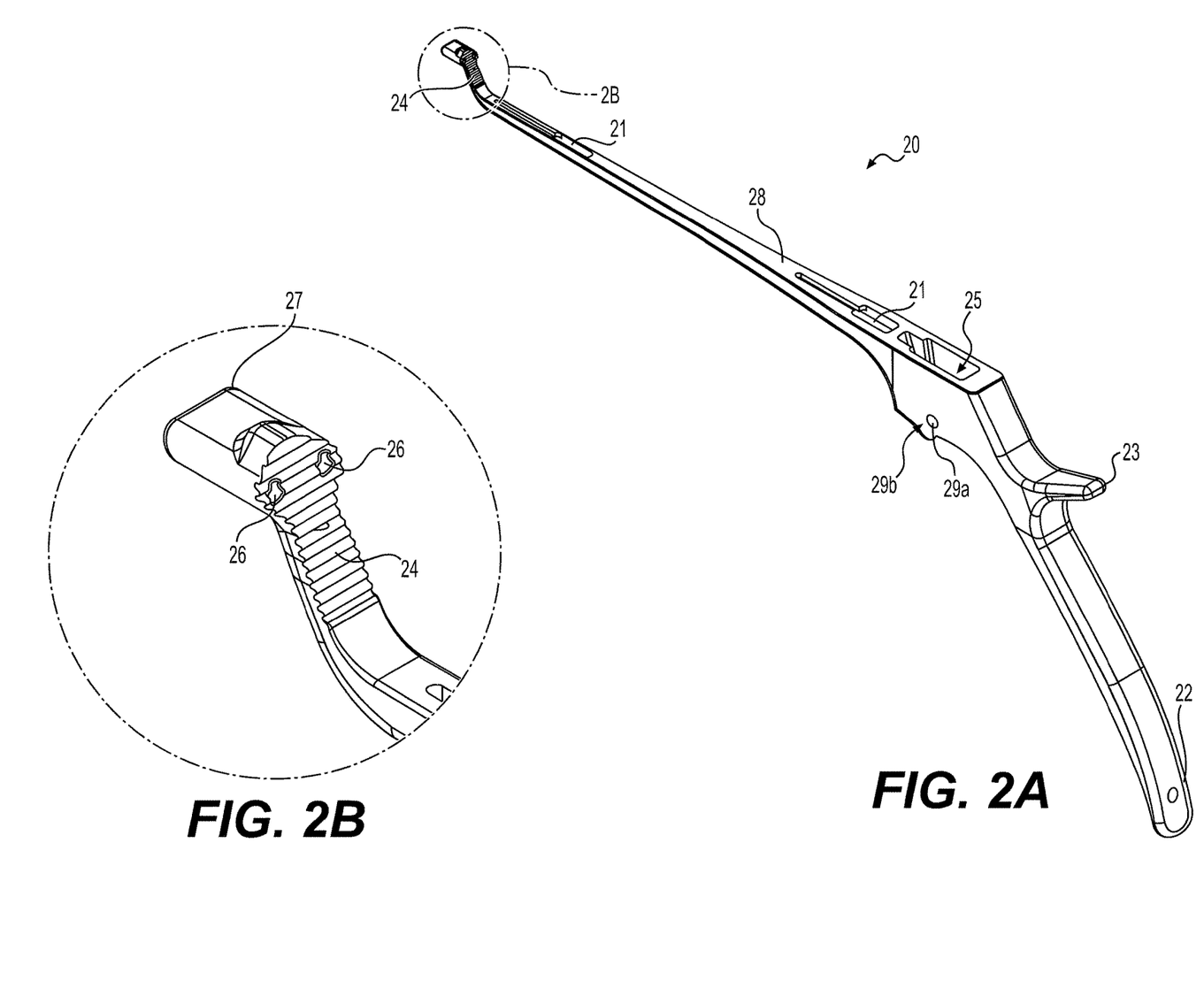
FIG. 2A is a perspective view of a static handle of the piercing forceps shown in FIG. 1.
FIG. 2B is a zoomed in perspective view of the distal tip of the static handle based on circle 2B shown in FIG. 2A

FIGS. 2A and 2B show an embodiment of a static handle 20 in greater detail. As shown, the static handle 20 can be generally L-shaped with a sliding surface 28 of the static handle 20 extending generally horizontally from the vertically extending grip 22. An upper portion of the grip 22 may define a proximally extending projection 23 upon which the user's thumb may be rested for added control. The sliding surface 28 can have front and rear guide channels 21. At least one of the guide channels 21 may have a T-shaped cross-section for accepting T-shaped guide posts of the primary slide 30 which can be slid distally into the T-shaped portion of the channels 21 for operation. A trigger opening 25 may extend through the static handle 20 for receiving an upper portion of the trigger 70 and dynamic handle 50. Hinge pin holes 29b may be located on either side of the trigger opening 25 for accepting a hinge pin 29a which engages the trigger 70 and dynamic handle 50. One of the hinge pin holes 29b may be threaded for threadedly engaging the hinge pin 29a.

Figures 9A, 9B:
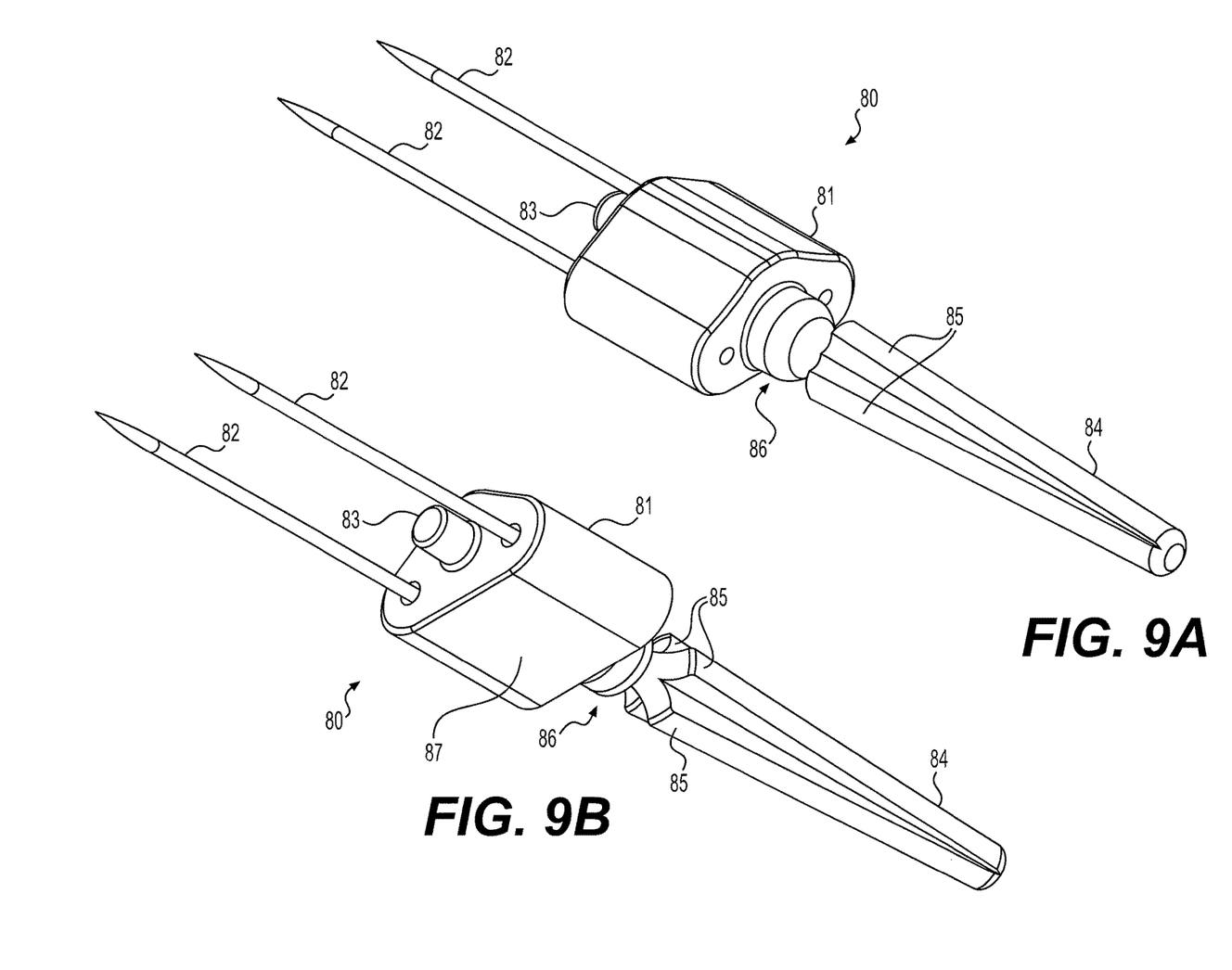
FIG. 9A is a top view of a needle cartridge for use with the piercing forceps shown in FIG. 1.
FIG. 9B is a bottom view of the needle cartridge for use with the piercing forceps shown in FIG. 1.

FIG. 2B details the distal tip and clamping surface 24 of the static handle 20. The distal tip of the static handle 20 may extend upwards to define a proximally facing clamping surface 24. The clamping surface 24 may be serrated or texturized to enhance tissue grip. A needle receptacle 27 may extend distally from the clamping surface 24 for accepting and surrounding the tips of the needles 82 of the needle cartridge 80 (an embodiment of a needle cartridge is shown in FIGS. 9A-9B). Two needle receptacle holes 26, which may be formed as blind holes, may extend through the clamping surface 24 and into the needle receptacle 27. The needle receptacle 27 can act to prevent unnecessary damage that may otherwise be caused by an exposed needle.

Figure 3:
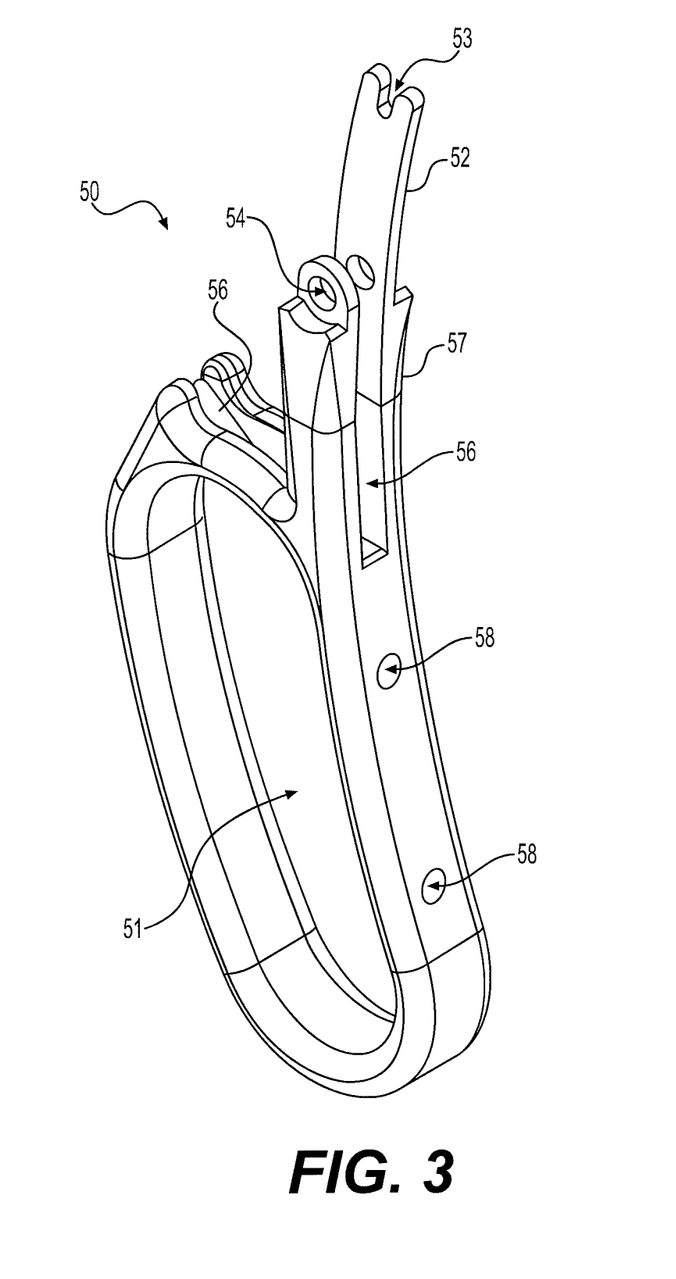
FIG. 3 is a perspective view of a dynamic handle of the piercing forceps shown in FIG. 1.

FIG. 3 shows an embodiment of a dynamic handle 50 for use on the forceps 10.

The dynamic handle 50 may define a finger opening 51 for accepting the fingers of a user. In some embodiments, the finger opening 51 may be designed to accept the middle, ring, and little fingers of a user, leaving the index finger to operate the trigger 70. A hinging arm 57 may extend up from a proximal side of the dynamic handle 50 and define a hinging hole 54 for accepting the hinge pin 29a. A lever arm 52 may extend up from the hinging arm 57 for engaging with and operating the primary slide 30. For example, a post extending from the primary slide 30 may be seated within a post slot 53 defined in the lever arm 52. As a result of the connection between the dynamic handle 50 and the primary slide 30, pivoting the lower portion of the dynamic handle 50 can push the primary slide 30 distally. Spring securing holes 58 may be provided in the dynamic handle 50 for connecting the trigger spring 64 and dynamic handle spring 62 using bolts or other suitable connectors known in the art.

An upper surface of the dynamic handle 50 defines a trigger groove 56 which extends through the hinging arm 57. When assembled, the trigger 70 may articulate within the trigger groove 56.

Figures 4A, 4B:
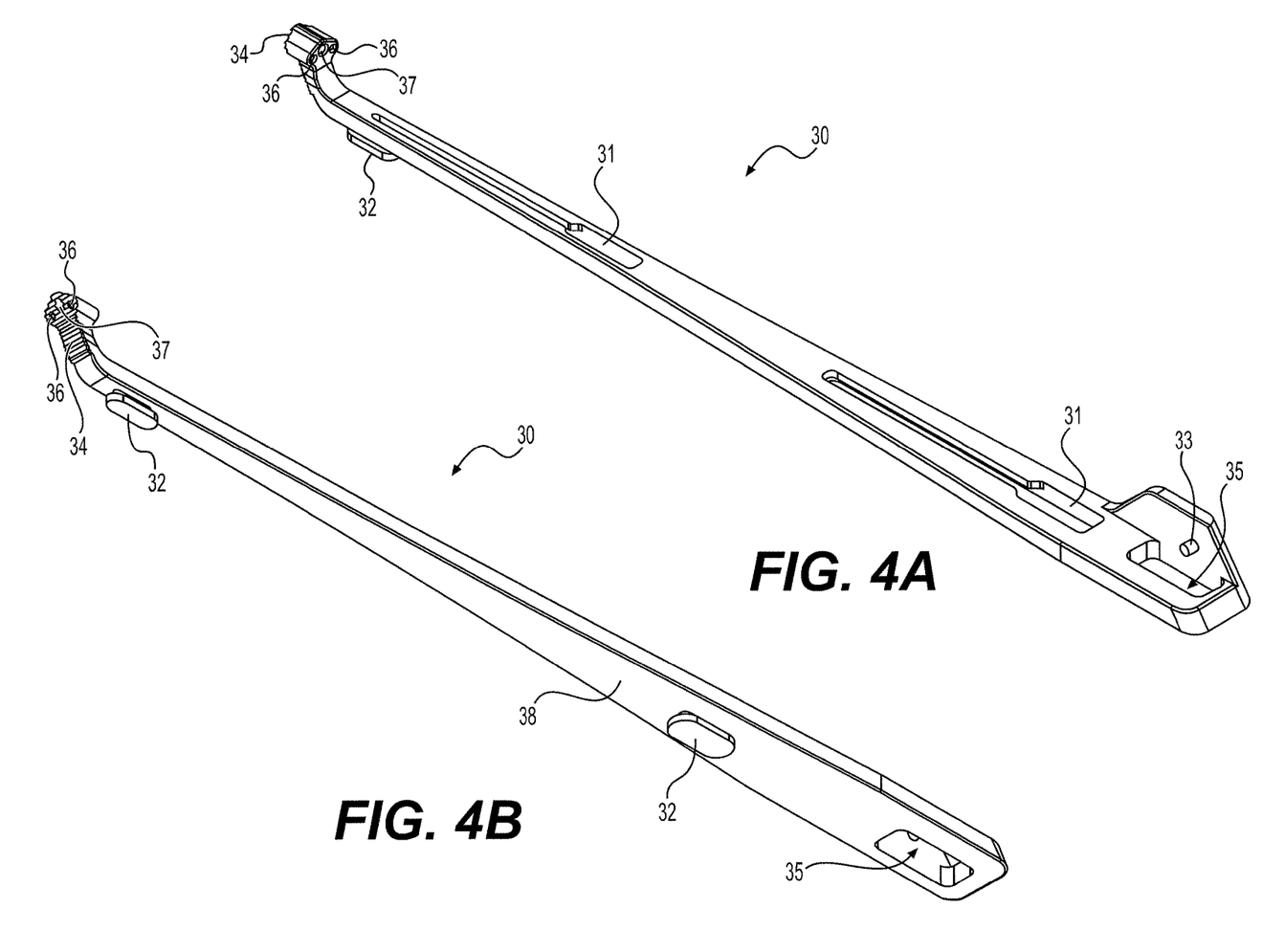
FIG. 4A is a top view of a primary slide of the piercing forceps shown in FIG. 1.
FIG. 4B is a bottom view of the primary slide of the piercing forceps shown in FIG. 1.

FIGS. 4A and 4B show an embodiment of a primary slide 30 in greater detail. The primary slide 30 may be designed to sit on top of the static handle 20 and slide distally or proximally based on movement of the connected dynamic handle 50. A lower side of the primary slide 30, as shown in FIG. 4B, may define a flat sliding surface 38 and two posts 32. The posts 32 may be designed to be inserted into the guide channels 21 defined in the static handle 30 for restricting movement between the static handle 20 and primary sliding member 30 to proximal and distal translation. The flat upper surface 28 of the static handle 20 slidably engages the flat lower surface 38 of the primary slide 30 to provide smooth operation. The distal end of the primary slide 30 may extend upwards to define a distally facing clamping surface 34. The clamping surface 34 may define serrations and/or may be texturized to assist in gripping tissue. The clamping surface 34 may be configured to align with the clamping surface 24 of the static handle 20 when the guide posts 32 are inserted into the guide channels 21.

Trigger opening 35 may be formed at a proximal end of the primary slide 30 for accepting an upper portion of the trigger 70, which engages the secondary slide 40. An elevated side wall may support a post 33 which extends partially across the trigger opening 35. When assembled, the post 33 may be contained within the post slot 53 formed in the lever arm 52 of the dynamic handle 50. An upper surface of the primary slide 30 may define guide channels 31 to guide movement between the primary slide 30 and secondary slide 40. In some embodiments, the guide channels 31 and posts of the secondary slide 40 may be T-shaped.

Needle guide holes 36 may be defined through the distal tip of the primary guide 30. The needle guide holes 36 can be positioned for allowing needles attached to the secondary slide 40 to extend through the primary slide 30, and associated clamping surface 36, to pierce tissue clamped between the primary slide 30 and static handle 20. Accordingly, the needle receptacle holes 26 in the static handle 20 and the needle guide holes 36 in the primary slide 30 can be aligned to accept needles attached to the secondary slide 40. An alignment post hole 37 may be defined between the needle guide holes 36 for aligning and stabilizing the needle cartridge 80 by accepting a guide post 30 of the cartridge 80.

Figures 5A, 5B:
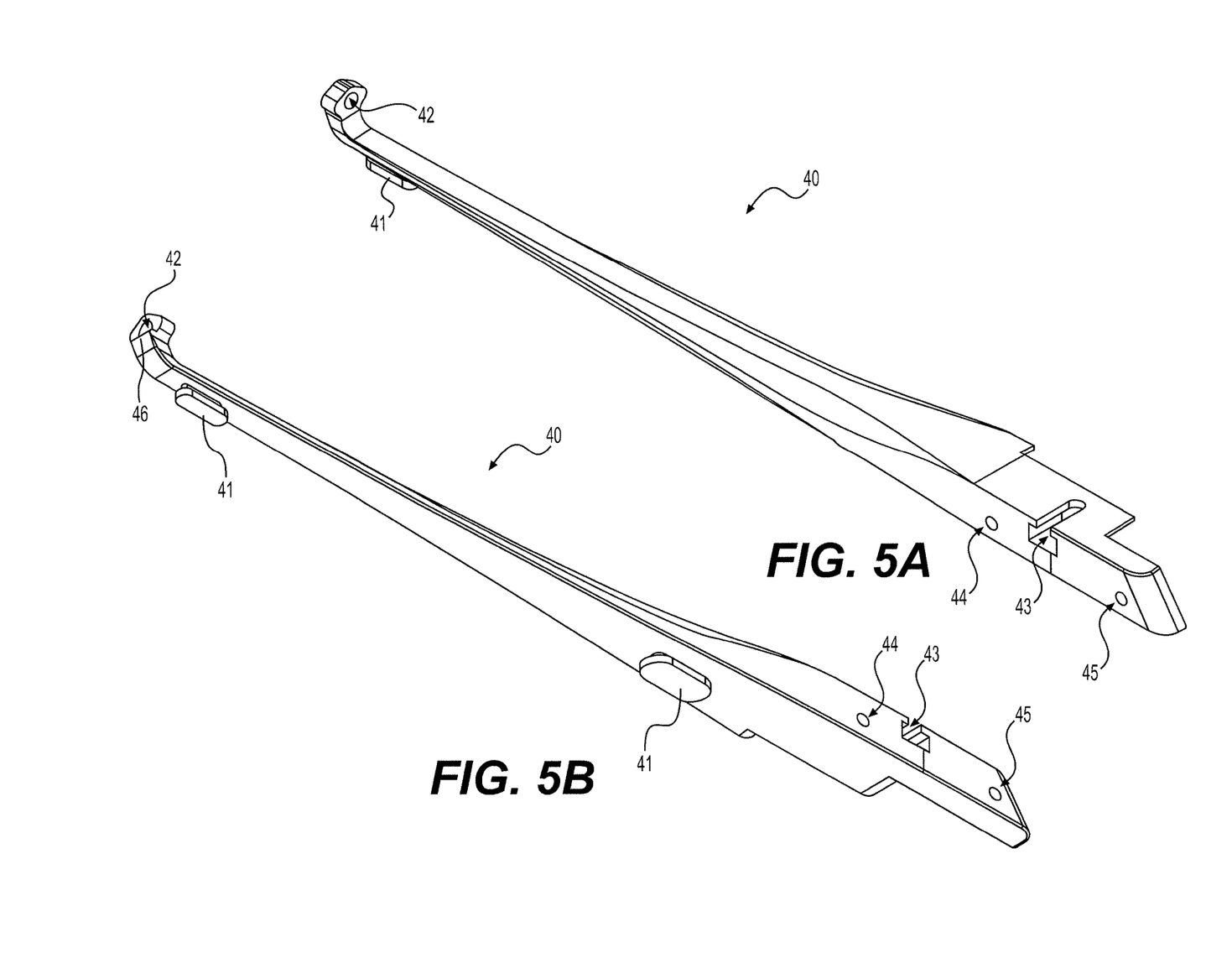
FIG. 5A is a top view of a secondary slide of the piercing forceps shown in FIG. 1.
FIG. 5B is a bottom view of the secondary slide of the piercing forceps shown in FIG. 1.

FIGS. 5A and 5B show an embodiment of a secondary slide 40 for use on the forceps 10. The secondary slide 40 may be designed to sit on top of the primary slide 30 and slide distally or proximally, relative to the primary slide 30, based on movement of the trigger 70. The secondary slide 40 may connect to the primary slide 30 through guide posts 41 that are accepted into guide channels 31 in the upper surface of the primary slide 30. The guide posts 41 and guide channels may be T-shaped. The distal tip of the secondary slide 40 may extend upwards to define a cartridge port 42 for accepting a needle cartridge 80. The needle cartridge 80 may be held at a proper alignment by a distally extending ledge 46 adjacent the cartridge port 42.

A pin aperture 45 may be defined in a flank of the secondary slide 40 near the proximal end. The pin aperture 45 may accept a removable pin of the pin spring 90 (shown in FIG. 7) which connects the secondary slide 40 to the trigger 70. A spring anchoring aperture 44 is located distal to the pin aperture 45 for securing the pin spring 90 to the secondary slide 40. A channel 43, e.g., T-shaped, may extend partially across the proximal end of the secondary slide 40 in a direction perpendicular to the proximal-distal axis. A slide pin 10 may be inserted into the T-shaped channel 43 for interfacing with a user's thumb.

Figure 6:
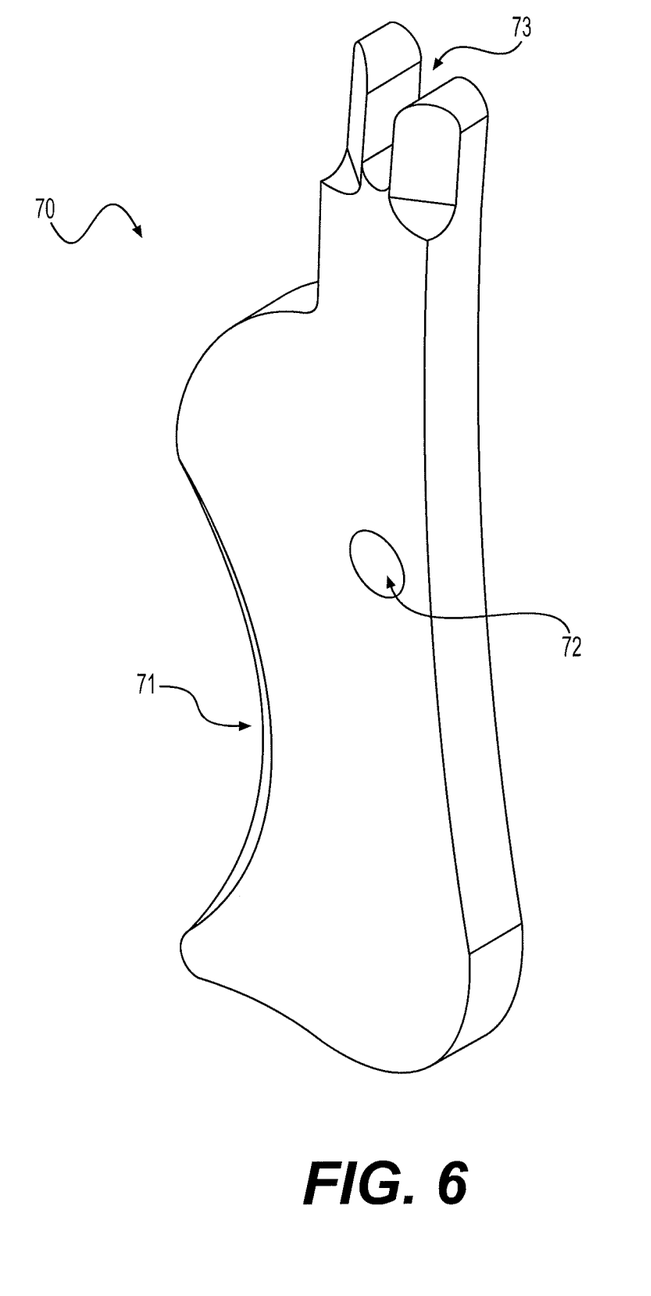
FIG. 6 is a perspective view of a trigger of the piercing forceps shown in FIG. 1.

FIG. 6 shows an embodiment of a trigger 70 in greater detail. A distal end of the trigger 70 may define a finger depression 71. The trigger may define a hinging aperture 72 for receiving the hinge pin 26a of the static handle 20 and acts as the pivot point of the trigger 70. An upper end of the trigger 70 may define a pin slot 73 that is designed to receive a pin of the pin spring 90. As previously discussed, an index finger of a user may pull on the finger depression 71 which will in turn pivot the pin slot 73 distally, thus moving the secondary slide 40 proximally via the pin spring 90. A lower end of the trigger 70 may be sized and shaped to fit within the trigger groove 56 of the dynamic handle 50.

Figure 7:
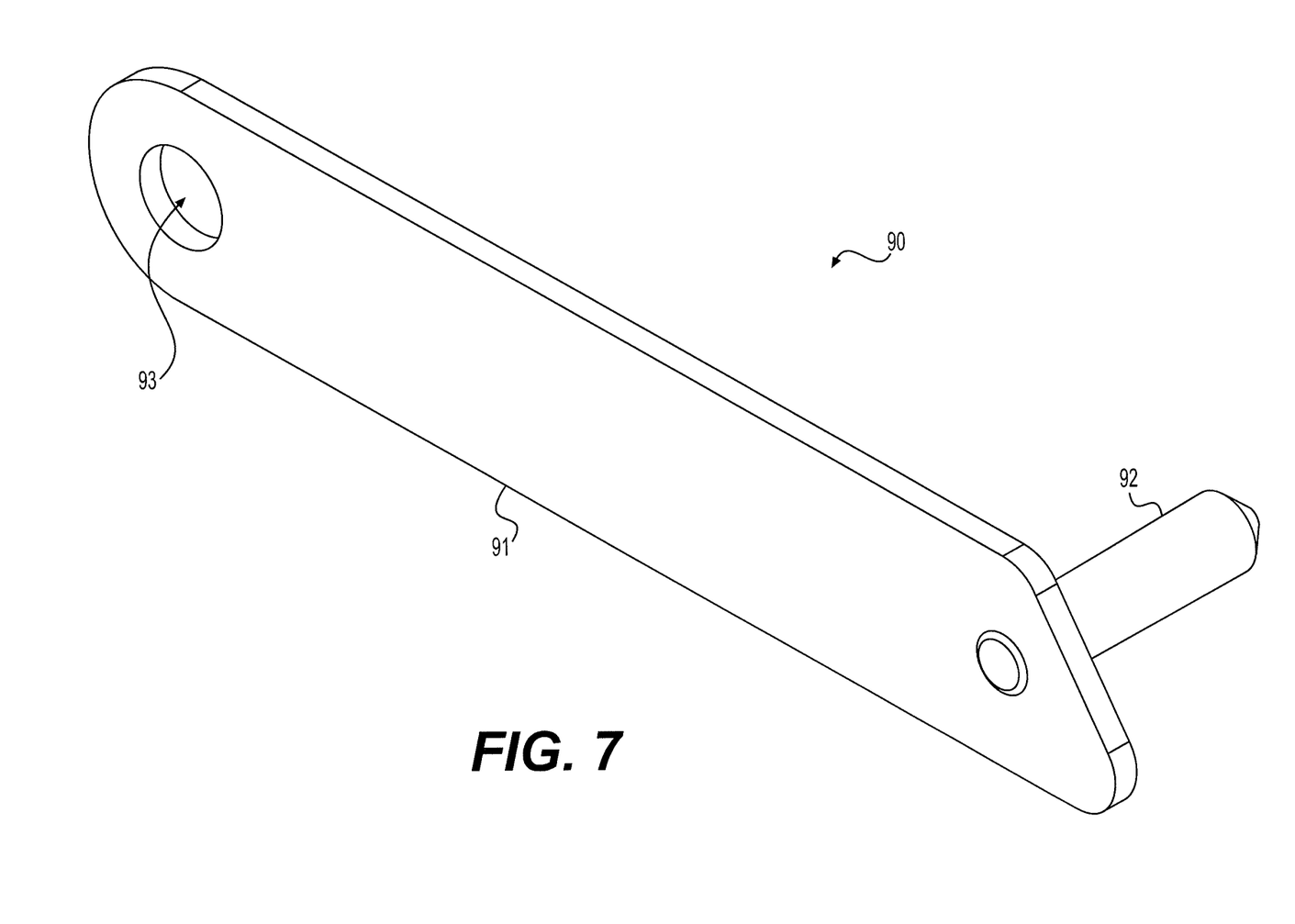
FIG. 7 is a perspective view of a pin spring of the piercing forceps shown in FIG. 1.

FIG. 7 shows an embodiment of a pin spring 90 which may be used on the forceps 10. The pin spring 90 may include a spring body 91 and a pin 92. The spring body 51 may define a screw receiving aperture 93 for connecting the pin spring 90 to the spring anchoring aperture 44 of the secondary slide 40. The flexibility of the body 91 allows the pin 92 to be removed from the pin aperture 45 of the secondary slide 40 for replacing the needle cartridge 80. For example, replacing a needle cartridge 80 may include first removing the pin 92 from the pin hole 45 by flexing the pin spring body 91 outwards, thus disconnecting the secondary slide 40 from the trigger 70. Then, the secondary slide 40 may be slid proximally until a needle cartridge 80 will fit between the distal end of the secondary slide 40 and the distal end of the primary slide 30. The needles of the needle cartridge 80 may then be inserted into the guide holes 36 of the primary slide 30, and the secondary slide 40 can be slide proximally until a snap-fit connection between the secondary slide 40 and cartridge 80 is achieved. Once the cartridge 80 is connected to the secondary slide 40, the pin 92 may be reinserted through the pin hole 45 and into the pin slot 73 of the trigger 70 for operation.

Figure 8:
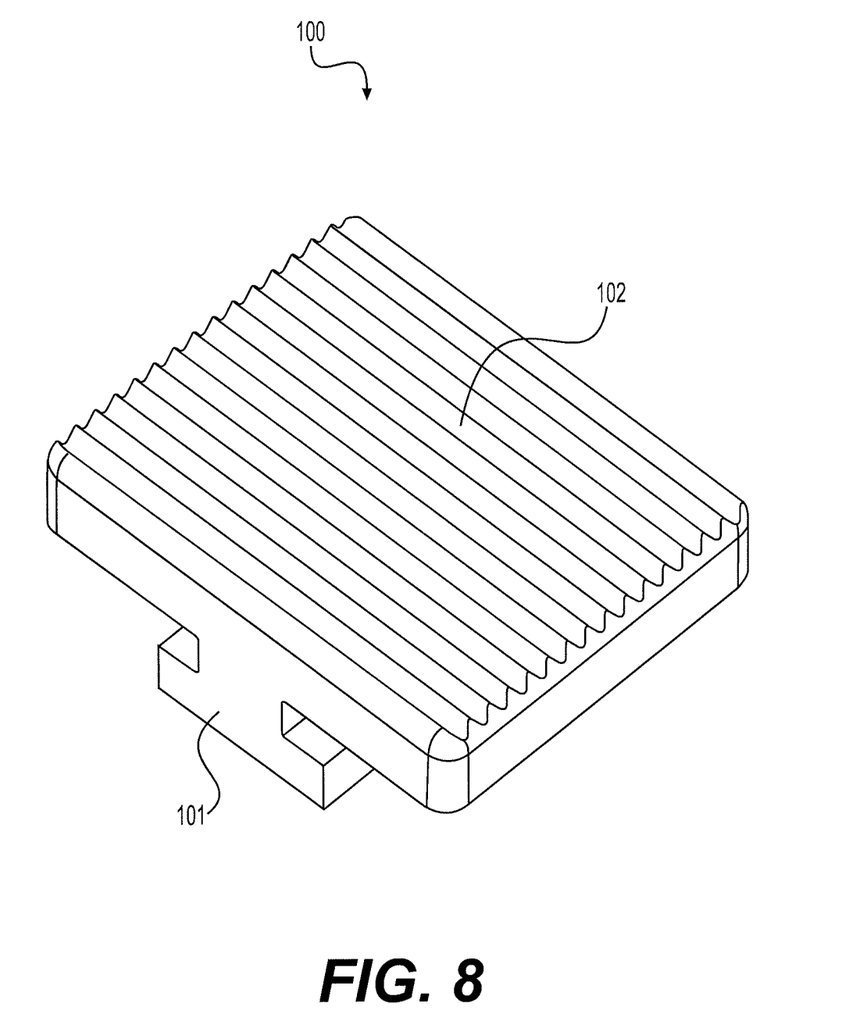
FIG. 8 is a perspective view of a grip block of the piercing forceps shown in FIG. 1.
Figure 10:
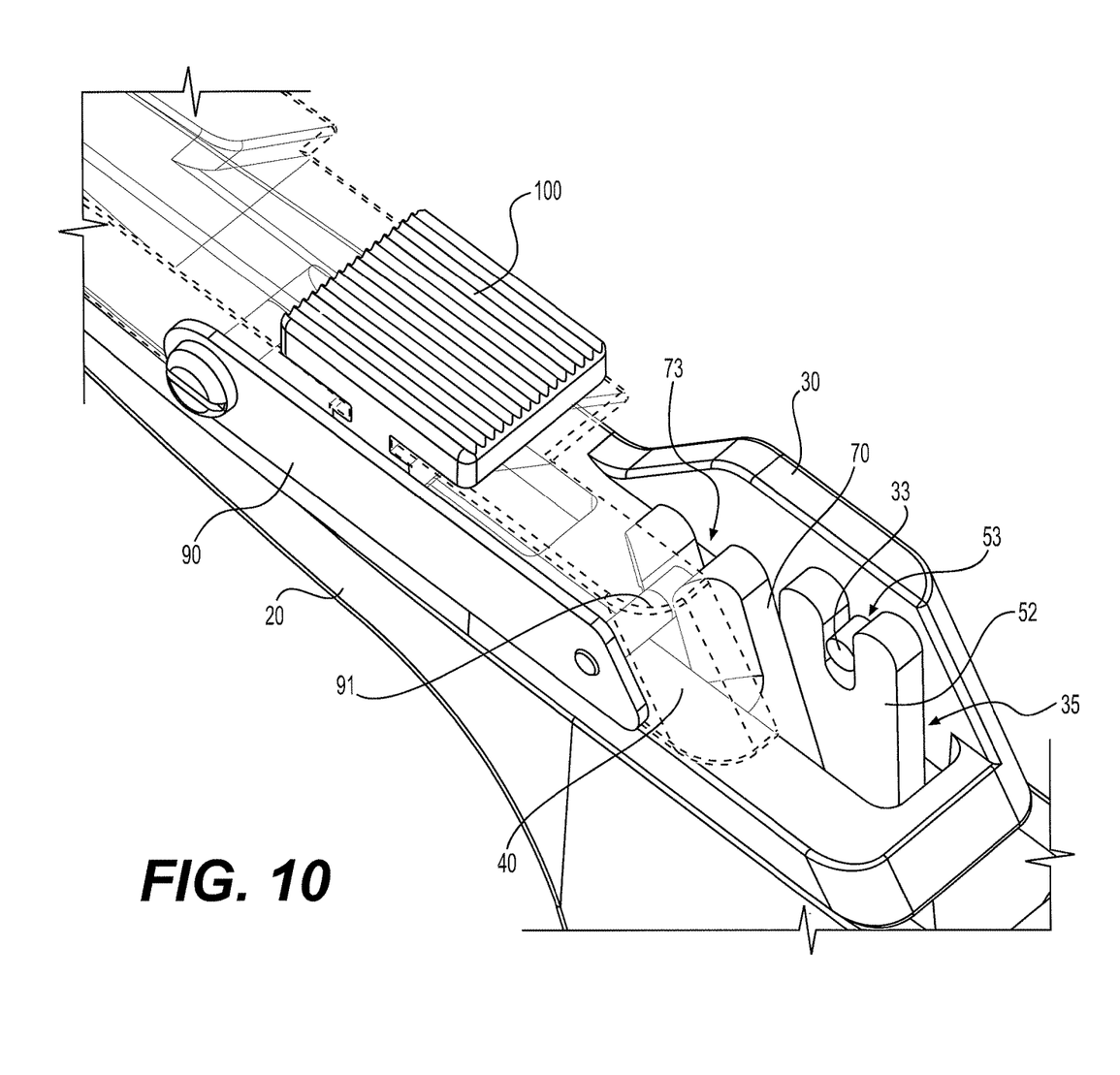
FIG. 10 is a zoomed in perspective view of the forceps of FIG. 1 detailing the interaction between the primary slide and dynamic handle, as well as the trigger and secondary handle.

FIG. 8 shows an embodiment of a grip block 100 which may be attached to the secondary slide 40 of the forceps 10. The grip block 100 may define a T-shaped post 101 which may be inserted into the T-shaped channel 43 of the secondary slide 40. An upper surface 102 of the grip block 100, opposite the T-shaped post 101, may be serrated or texturized to provide friction against a user's thumb during operation. The grip block 100 may be used to control movement of the secondary slide 40 when the secondary slide 40 has been disconnected from the trigger 70 by disengaging the spring pin 90. The gripping block 100 may be held in place by the spring pin 90, as seen in FIG. 10.

FIGS. 9A and 9B show an embodiment of a needle cartridge 80 which may be used with the forceps 10. Two needles 82 may extend proximally out from a body 81 of the cartridge 80. The needles 82 may be positioned to align with the needle guide holes 36 of the primary slide 30 and needle receptacles 26 of the static handle 20 when the needle cartridge 80 is inserted into the cartridge port 42 of the secondary slide 40. The cartridge body 81 may define a lower planar surface 87 to interface with a ledge 46 adjacent the cartridge port 42 to hold the cartridge 80 at the proper angular alignment. An alignment post 83 may extend distally out from the cartridge body 81 to align and stabilize the cartridge 80 by extending into an alignment post hole 37 in the primary slide 30 when the secondary slide 40 is in a distal position.

The needle cartridge 80 may be designed for single use and therefore can be designed to be removably connected to the cartridge port 42 of the secondary slide 40. A connecting tail 84 may extend proximally from the cartridge body 81. The connecting tail may define multiple tapered flairs 85 which taper out as they extend distally. A neck 86 is defined between the flairs 85 and the body 81 to provide for a snap-fit connection.

The cartridge 80 may be connected to the secondary slide 40 by inserting the needles 82 into the needle guides 36 of the primary slide 30. The secondary slide 40 may then be slid distally to receive the cartridge tail 84 in the cartridge port 42. The flairs 85 may compress inwards as the tail 84 proceeds through the port 42, and then snap back out when the port 42 reaches the neck 86, resulting in a snap-fit connection. The cartridge 80 may be removed by pushing distally on the tail 84.

In some embodiments, the cartridge 80 may define single needle 82 or more than two needles 82. Accordingly, the primary slide 30 may define a respective amount of needle guides 36 and the static handle 20 may define a respective amount of needle receptacles 26.

FIG. 10 shows an embodiment of the connection between the dynamic handle 50 and primary slide 30, as well as the connection between the trigger 70 and secondary slide 40, when the trigger 70 is being depressed. Both the lever arm 52 of the dynamic handle 50 and the upper end of the trigger 70 extends through the trigger opening 35 of the primary slide 30. The post slot 53 on the lever arm is engaged with the post 33 of the primary slide 30. The pin slot 73 of the trigger 70 is engaged with the pin 91 of the pin spring 90 which is connected to the secondary slide 40. As seen in FIG. 10, the trigger opening 35 provides space for the trigger 70 to be pivoted irrespective of the primary slide 30.

Figures 11A, 11B:
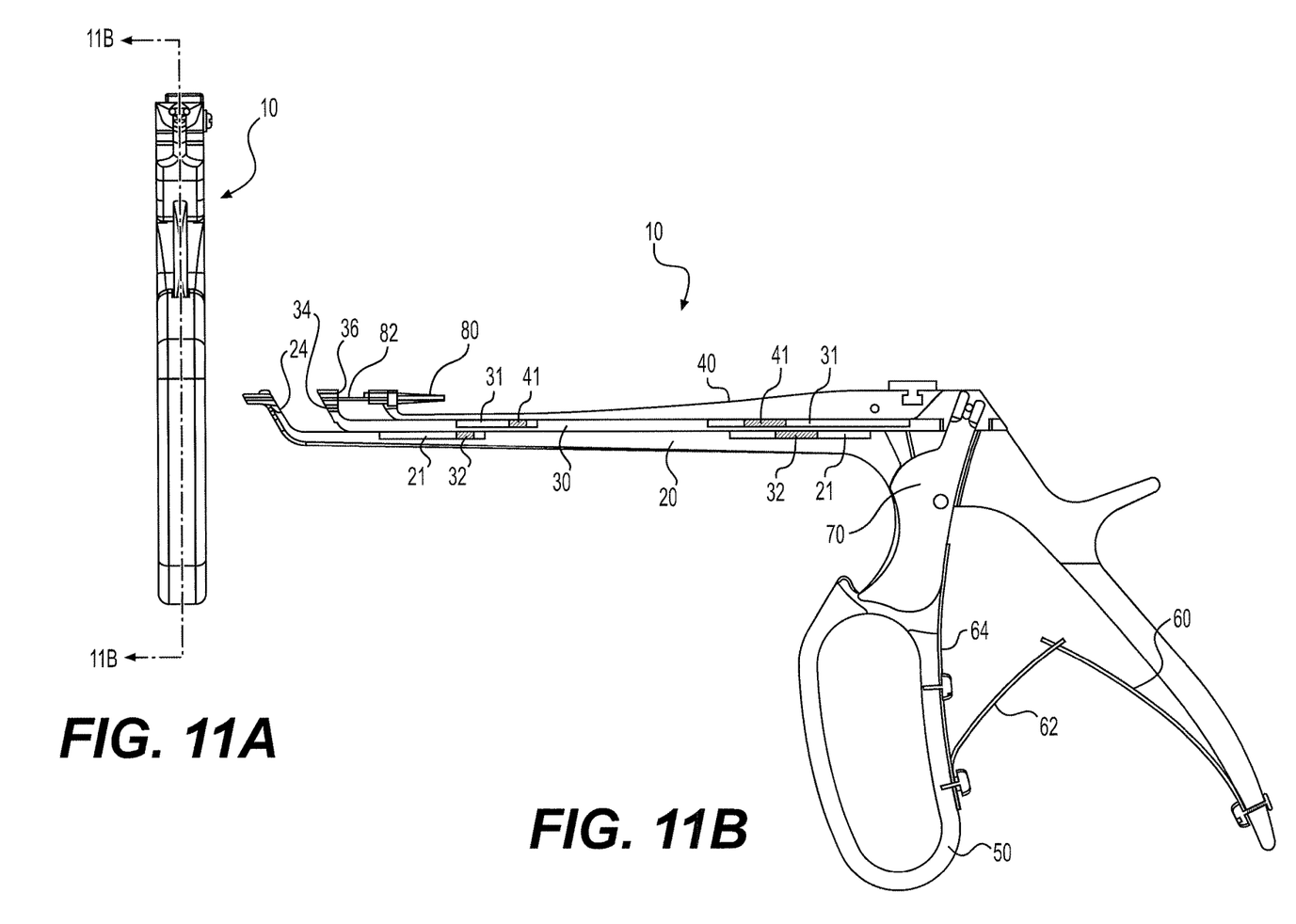
FIG. 11A shows a rear view of the forceps of FIG. 1 providing cross-section line 11B on which the cross-sections shown in FIGS. 11B-11D are taken.
FIG. 11B shows a sectioned side view of the forceps of FIG. 1, taken along line 11B shown in FIG. 11A, having the dynamic grip and trigger in a distal, resting position.
Figure 11C:
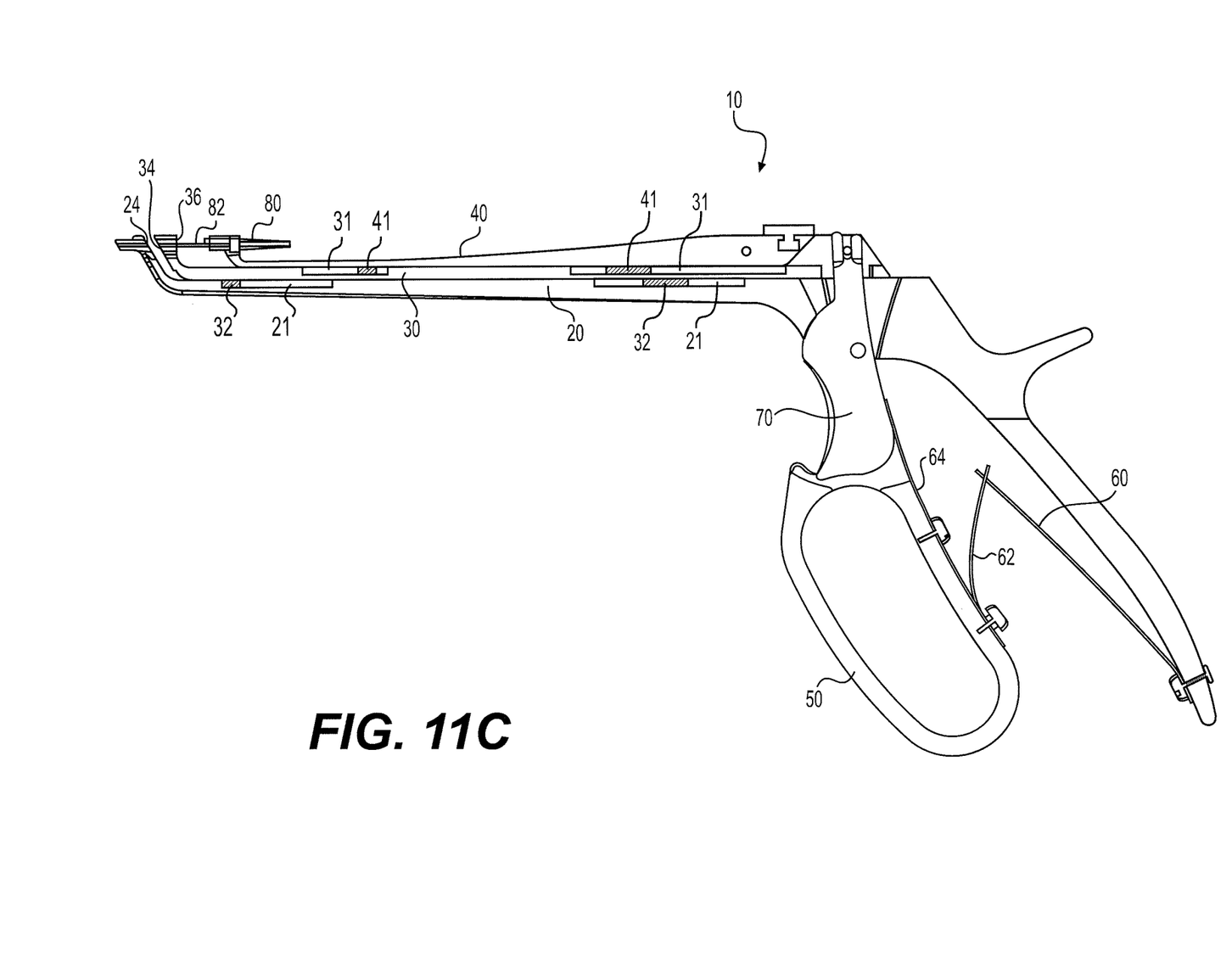
FIG. 11C shows a sectional side view of the forceps of FIG. 1, taken along line 11B shown in FIG. 11A, having the dynamic grip in a proximal, actuated position.
Figure 11D:
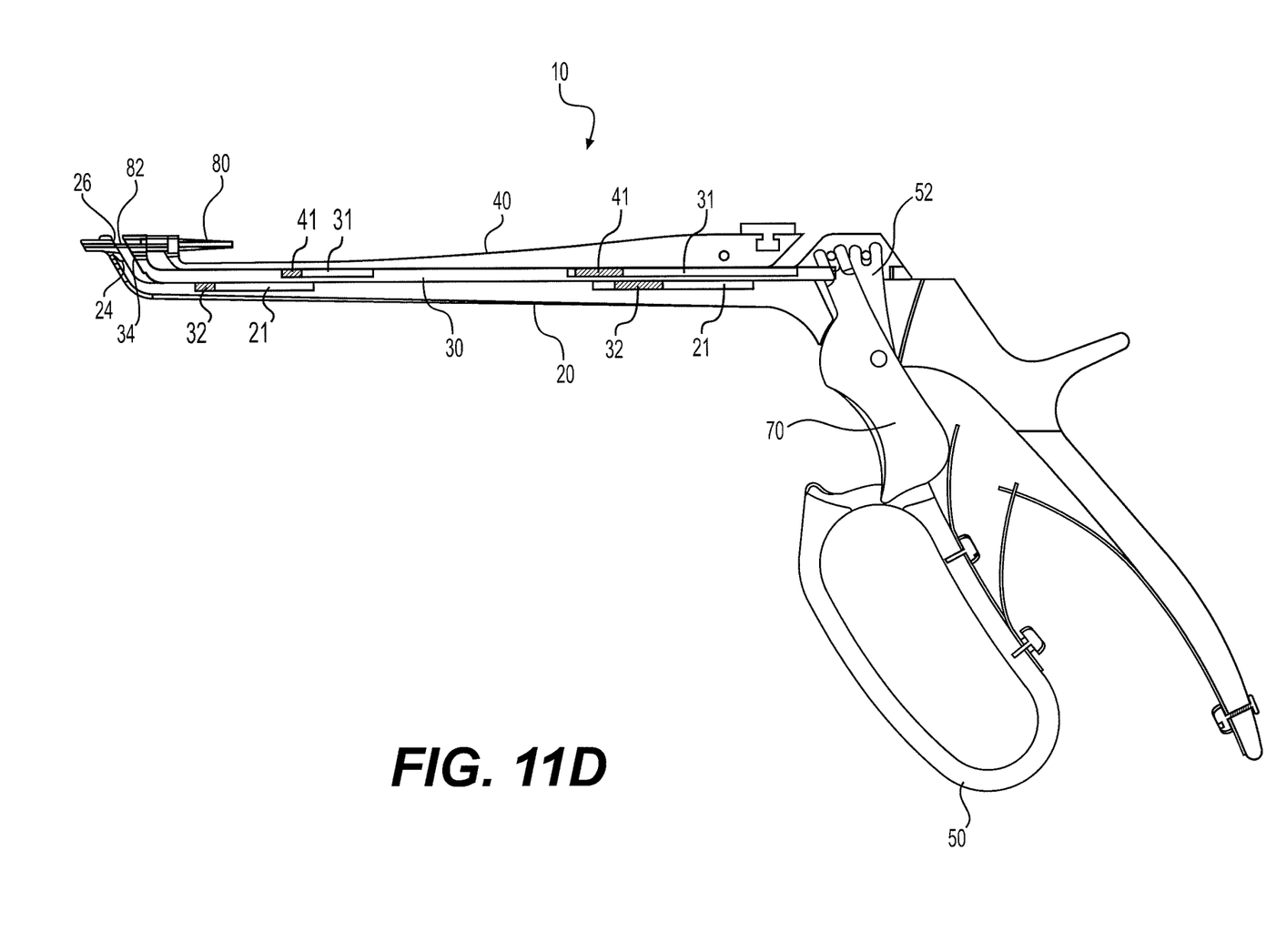
FIG. 11D shows a sectional side view of the forceps of FIG. 1, taken along line 11B shown in FIG. 11A, having the dynamic grip and trigger in a proximal, actuated position.

FIGS. 11A-D show the interaction between the components of the forceps 10 during an act of clamping and piercing based on the cross-section taken at line 11B shown in FIG. 11A. FIG. 11B shows the forceps 10 in a resting position where the springs 60, 62, 64 are holding the primary 30 and secondary 40 slides at a proximal position. FIG. 11C shows the forceps 10 once the dynamic handle 50 has been pulled proximally to draw the clamping surfaces 24, 34 of the static handle 20 and primary member 30 toward each other for clamping tissue therebetween. In this position, the secondary slide 40 remains in a proximal position relative to the primary slide 30, and the needles 82 do not extend past the needle guides 36 of the primary slide 30. FIG. 11D shows the forceps 10 with the dynamic handle 50 and trigger 70 pulled. In this position, tissue between the clamping surfaces 24, 34 will be secured by clamping forces, as well as the two needles 82 piercing the tissue. By additionally securing the tissue with the needles 82, the tissue can remain secured while clamping forces are reduced, thus reducing the chance of damaging the tissue through clamping.

It is to be understood that the piercing forceps is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A piercing forceps, comprising:
   a generally L-shaped static handle including a distal tip, a proximal grip, and an upper surface;
   a primary slide slidably engaged with the upper surface of the static handle, the primary slide including a distal tip, a proximal post, and an upper surface;
   a secondary slide slidably engaged with the upper surface of the primary slide, the secondary slide including a proximal tip, a distal end, and a hinge pin;
   a dynamic handle pivotally attached to the static handle, the dynamic handle defining a lever arm, the lever arm engaging the post of the primary slide;
   a trigger pivotally attached to the static handle, the trigger engaging the hinge pin of the secondary slide; and
   at least one needle extending from the distal end of the secondary slide;
   wherein pulling the dynamic handle draws the distal tip of the primary slide toward the distal tip of the static handle, and pulling the trigger advances the at least one needle through the distal tip of the primary slide and the distal tip of the static handle.

2. The piercing forceps of claim 1, wherein the distal tip of the static handle includes a proximally facing gripping surface and the distal tip of the primary slide includes a distally facing gripping surface, the gripping surface of the static handle and the gripping surface of the primary slide being configured to grip tissue clamped therebetween.

3. The piercing forceps of claim 2, wherein the gripping surface of the static handle and the gripping surface of the primary slide are serrated or textured to assist in gripping tissue clamped between the gripping surfaces.

4. The piercing forceps of claim 1, wherein the pin of the secondary slide is retractable for disengaging the secondary slide and trigger.

5. The piercing forceps of claim 4, further comprising a spring configured to press the pin into the secondary slide.

6. The piercing forceps of claim 1, wherein the at least one needle is provided on a needle cartridge, the needle cartridge being removably attachable to a needle cartridge port defined in a distal top of the secondary slide.

7. The piercing forceps of claim 1, wherein the distal tip of the static handle defines at least one needle receptacle for receiving the at least one needle when the secondary slide is in a distal position, the at least one needle receptacle being a blind hole.

8. The piercing forceps of claim 1, wherein the distal tip of the primary slide defines at least one needle guide extending therethrough for receiving the at least one needle when the secondary slide is in a distal position.

9. The piercing forceps of claim 1, further comprising a primary spring, the primary spring configured to press the dynamic handle away from the grip of the static handle.

10. The piercing forceps of claim 1, further comprising a trigger spring, the trigger spring configured to press the trigger proximally relative to the dynamic handle.

11. The piercing forceps of claim 1, further comprising a guide peg between the static handle and the primary slide, for restricting movement between the static handle and primary slide to a proximal-distal direction.

12. A piercing forceps, comprising:
    a static handle and a primary slide, the static handle and primary slide being slidably engaged;
    a secondary slide slidably engaged with the primary slide;
    a dynamic handle configured to slide the primary slide along a length of the static handle;
    a trigger configured to slide the secondary slide along a length of the primary slide; and
    at least one needle configured to extend through the primary slide and secondary slide when the trigger is actuated.

13. The piercing forceps of claim 12, wherein the static handle defines a first gripping surface and the primary slide defines a secondary gripping surface, the forceps being configured to clamp tissue between the first gripping surface and the second gripping surface when the dynamic handle is actuated.

14. The piercing forceps of claim 13, wherein the static handle defines at least one needle receptacle for receiving the at least one needle when the trigger is actuated, the at least one needle receptacle being a blind hole.

15. The piercing forceps of claim 13, wherein the primary slide defines at least one needle guide extending therethrough for receiving the at least one needle when the trigger is actuated.

* * * * *